(12) United States Patent
Titus et al.

(10) Patent No.: US 8,501,098 B1
(45) Date of Patent: Aug. 6, 2013

(54) TEMPORALLY ADDRESSABLE DETECTION ARRAY

(75) Inventors: Albert H. Titus, Buffalo, NY (US); Frank V. Bright, Williamsville, NY (US); Alexander N. Cartwright, Williamsville, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 137 days.

(21) Appl. No.: 10/945,344

(22) Filed: Sep. 20, 2004

Related U.S. Application Data

(60) Provisional application No. 60/503,915, filed on Sep. 18, 2003.

(51) Int. Cl.
*G01N 21/00* (2006.01)

(52) U.S. Cl.
USPC ............. 422/82.05; 422/82.06; 422/82.07; 436/164; 436/165; 436/172

(58) Field of Classification Search
USPC ............. 422/55, 68.1, 82.05, 82.06, 82.07, 422/82.09, 82.11, 83, 85; 436/164, 165, 172
See application file for complete search history.

(56) References Cited

U.S. PATENT DOCUMENTS

| | | | | |
|---|---|---|---|---|
| 4,759,210 A | * | 7/1988 | Wohltjen | 73/31.07 |
| 5,073,029 A | * | 12/1991 | Eberly et al. | 356/432 |
| 5,500,188 A | * | 3/1996 | Hafeman et al. | 204/403.01 |
| 5,512,490 A | * | 4/1996 | Walt et al. | 436/171 |
| 5,622,868 A | * | 4/1997 | Clarke et al. | 436/147 |
| 5,650,311 A | * | 7/1997 | Avnir et al. | 435/176 |
| 5,786,219 A | * | 7/1998 | Zhang et al. | 436/523 |
| 5,812,272 A | * | 9/1998 | King et al. | 356/445 |
| 5,936,730 A | * | 8/1999 | Foley et al. | 356/344 |
| 5,994,150 A | * | 11/1999 | Challener et al. | 436/518 |
| 6,078,705 A | * | 6/2000 | Neuschafer et al. | 385/12 |
| 6,331,438 B1 | * | 12/2001 | Aylott et al. | 436/172 |
| 6,368,558 B1 | * | 4/2002 | Suslick et al. | 422/55 |
| 6,488,891 B2 | * | 12/2002 | Mason et al. | 422/58 |
| 6,492,182 B1 | * | 12/2002 | Bright et al. | 436/172 |
| 6,495,102 B1 | * | 12/2002 | Suslick et al. | 422/55 |
| 6,649,416 B1 | * | 11/2003 | Kauer et al. | 436/164 |
| 6,680,206 B1 | * | 1/2004 | McDevitt et al. | 436/172 |
| 6,707,539 B2 | * | 3/2004 | Selinfreund et al. | 356/71 |
| 6,890,764 B2 | * | 5/2005 | Chee et al. | 436/518 |

* cited by examiner

*Primary Examiner* — Jill Warden
*Assistant Examiner* — Dwayne K Handy
(74) *Attorney, Agent, or Firm* — Hodgson Russ LLP

(57) ABSTRACT

A detection device and a method of detection are disclosed. The device may have a sensor array, a detector array, and a sensor controller. The sensor array may have a plurality of sensors, each sensor being responsive to a different analyte of interest. Each sensor may also be able to emit electromagnetic energy. For example, one or more of the sensors may include an LED. One or more of the sensors may include a sensing compound within a xerogel, which is responsive to an analyte of interest. In the method, one of the sensors is turned on, and one or more of the detectors are activated to receive electromagnetic energy emitted from the sensor.

13 Claims, 9 Drawing Sheets

TEMPORALLY ADDRESSABLE DETECTION ARRAY

CROSS-REFERENCE TO RELATED APPLICATION

This application claims the benefit of priority to U.S. provisional patent application Ser. No. 60/503,915, filed on Sep. 18, 2003.

FIELD OF THE INVENTION

The present invention relates to devices and methods for detecting analytes in a sample.

BACKGROUND OF THE INVENTION

A standard detection system places a sample in contact with a sensor array platform, and the output from the sensor array platform is detected by a charged coupled device ("CCD") camera. Unfortunately, CCDs require multiple voltages, they can consume significant electrical power and they require additional post-processing to determine the changes in signals from a given sensor element.

Existing optically-based devices for detecting the presence of analytes, including CCDs, have a configuration whereby all sensor and detector elements are either "on" or "off". In addition, despite several well-documented advantages, there has not been a marriage of complementary metal oxide semiconductor ("CMOS") optical array detectors with discrete or arrayed sensors having a light emitting diode ("LED") and a xerogel-based sensing compound.

SUMMARY OF THE INVENTION

The present invention includes a detection device having a sensor array, a detector array, and a sensor controller. The sensor array may have a plurality of sensors, each sensor being responsive to a different analyte of interest. Each sensor may also be able to emit electromagnetic energy. For example, one or more of the sensors may include an LED. One or more of the sensors may include a sensing compound within a xerogel, which is responsive to an analyte of interest.

The sensor controller may be in communication with the sensor array. The sensor controller may be able to turn on at least one of the sensors so as to emit electromagnetic energy while another of the sensors is turned off, so as not to emit electromagnetic energy. For example, the sensor controller may turn on one sensor at a time.

The detector array may have a plurality of detectors. One or more of the detectors may be able to receive emitted electromagnetic energy from one or more of the sensors. A receiver may be in communication with the detector array. The receiver may obtain signals from all the detectors when a sensor is turned on, or the receiver may obtain a signal from only one of the detectors when a particular sensor is turned on.

A device according to the invention may include one or more filters. The filter may receive the electromagnetic energy, and some of that energy may be allowed to pass through the filter with relatively little attenuation, compared to other portions of the electromagnetic energy received. One or more of the filters may be tunable, so that the portion of energy passing through the filter with little or no attenuation may be changed. Filters may be provided so that energy from more than one sensor is filtered by a single filter, or so that energy from only one of the sensors reaches a particular filter.

In a method according to the invention, a determination may be made as to whether an analyte of interest is in a sample. In such a method, a device may be provided having a sensor array, a detector array, a sensor controller in communication with the sensor array, and a receiver in communication with the detector array. The sensor array may be contacted with a sample to be analyzed. An input signal from the sensor controller to a first one of the sensors may be provided, which when received by the first sensor, causes the first sensor to emit electromagnetic energy. The electromagnetic energy may be received at the detector array, and a corresponding signal may be provided to the receiver. The signal provided to the receiver may be provided by only one of the detectors, or the signal may be provided by more than one of the detectors. The receiver may then identify the signal as being related to the first sensor. The signal may then be analyzed to determine whether the analyte is in the sample.

BRIEF DESCRIPTION OF THE DRAWINGS

For a fuller understanding of the nature and objects of the invention, reference should be made to the accompanying drawings and the subsequent description. Briefly, the drawings are.

FURTHER DESCRIPTION OF EMBODIMENTS OF THE INVENTION

Figure 1:
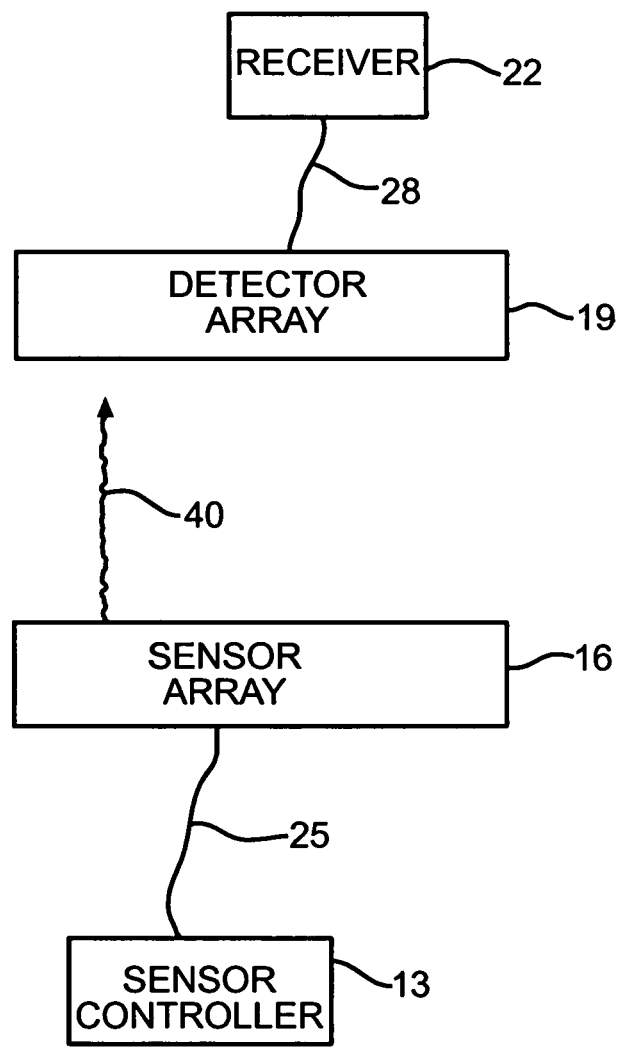
FIG. 1, which illustrates a device according to the invention.

FIG. 1 depicts a detection device 10 according to the invention having a sensor controller 13, a sensor array 16, a detector array 19 and a receiver 22. The sensor controller 13 and the sensor array 16 have an input communication channel 25 which enables signals from the sensor controller 13 to reach the sensor array 16. The detector array 19 and the receiver 22 have an output communication channel 28 which enables signals from the detector array 19 to reach the receiver 22.

Figure 2:
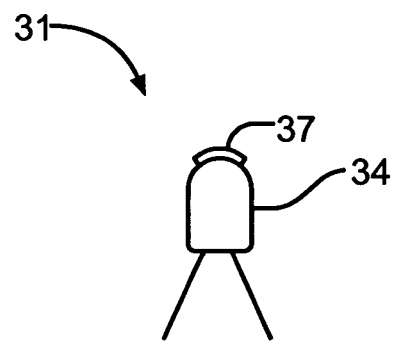
FIG. 2, which illustrates a sensor that may be used in a device according to the invention.
Figure 3:
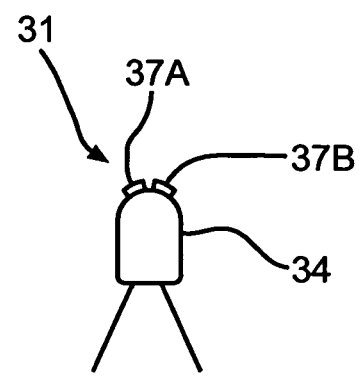
FIG. 3 which illustrates a sensor that may be used in a device according to the invention.

The sensor array 16 may have more than one sensor 31. A sensor 31 may have an LED 34 and one or more sensor compounds 37. FIG. 2 depicts such a sensor 31. Each sensor compound 37 may be chemically sensitive to a different analyte of interest. The LED 34 and one sensor compound 37 may be thought of as a single sensor 31. However, it should be noted that a single LED 34 may be used in conjunction with more than one sensor compound 37 to form multiple sensors 31. FIG. 3 depicts such a sensor 31 having a first sensor compound 37A and a second sensor compound 37B. It may also be possible to form the sensor array 16 from sensors 31 that each have one LED 34 per sensor compound 37.

As an example, a single LED 34 and a single sensor compound 37 may be used to form a sensor 31, and if the sensor array 16 were composed of 100 such sensors 31 each having a diameter of 100 micrometers, the sensors 31 might be formed in a 10×10 array and spaced on 150 micrometer centers. A corresponding detector array 19 might comprise a 10×10 array of 100 micrometer diameter CMOS detectors spaced on 150 micrometer centers.

The LED 34 may serve to provide a source of electromagnetic energy to the sensor compound 37. In the presence of the analyte of interest and the electromagnetic energy, the sensor compound 37 may exhibit characteristics that are not present when either the analyte or the electromagnetic energy, or both, are not present. For example, the sensor compound 37 may fluoresce when the analyte is present and electromagnetic energy is provided to the sensor compound 37. There are many such sensor compounds 37, and some of them may be purchased from Sigma-Aldrich, Inc. The amount of fluorescence from a given sensor 31 may be a function of the concentration of the analyte in the sample.

Figure 4:
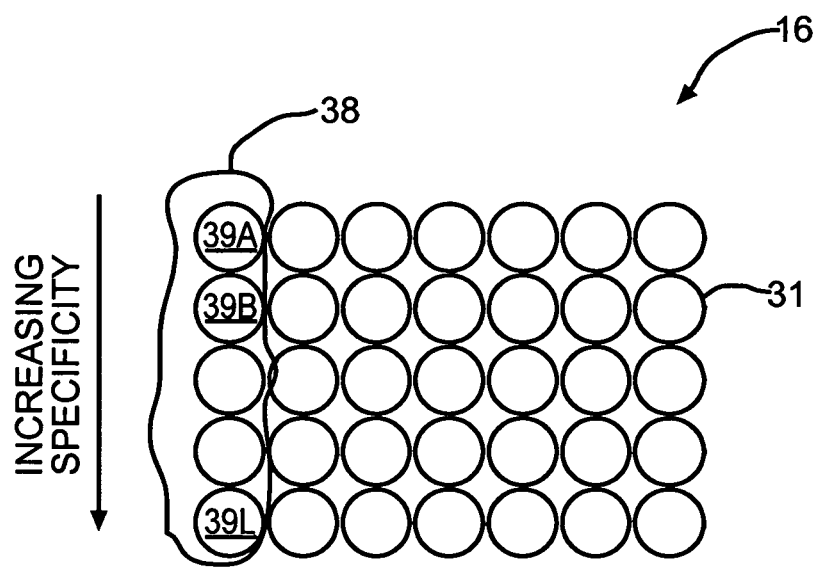
FIG. 4, which illustrates a sensor array according to the invention.

The sensors 31 in sensor array 16 may be arranged in a logical order. For example, FIG. 4 depicts a sensor array 16 in which a first set 38 of sensors 31 are designed to detect a particular type of analyte, and sensors within that set 38 may be arranged so that the specificity of the sensors 31 changes. For example, a first sensor 39A in the set 38 might be responsive to the presence of many different analytes within a class of analytes, the second sensor 39B might be responsive to a subset of those analytes, and so on until the last sensor 39L in the set 38 is responsive to only one or two analytes within the class of analytes.

The detector array 19 may be provided to receive the electromagnetic energy 40 emitted from the sensor 31. The detector array 19 may have a plurality of detectors 43, some or all of which may be CMOS optical detectors. The detector array 19 may provide an analog output from each detector 43 to be read out directly by the receiver 22.

To determine the presence of a particular analyte, say analyte "X", an X-responsive sensor "$S_x$" may be provided, and a corresponding detector "$D_x$" may be provided. In a similar manner, to determine the presence of analyte "Y", a Y-responsive sensor "$S_Y$" may be provided, and a corresponding detector "$D_Y$" may be provided. In this fashion, a "one-to-one match" between each sensor 31 and each detector 43 may be established. Such a design may require accurate alignment of the sensor array 16 and detector array 19 so that electromagnetic energy 40 from each sensor 31 may be received by the corresponding detector 43.

The relative positions of $D_X$ and $S_x$ may need to be positioned to prevent cross-talk. For example, assuming the analyte of interest is analyte "X", $D_X$ may be positioned relative to other detectors 43 so that $D_X$ receives detectably more energy from $S_X$ than the other detectors 43. Alternatively, or in addition, $S_X$ may be positioned relative to other sensors so that D, receives more energy from $S_x$ than the other detectors 43. A lens or lenslet array may be used to focus energy 40 from a particular sensor 31 to its corresponding detector 43, and in this fashion, the detectors 43 may be placed closer together, the sensors 31 may be placed closer together, or both.

The energy 40 emitted from a particular sensor 31 may not be uni-directional. For example, if each sensor 31 has a corresponding detector 43, each detector 43 might receive energy from a number of neighboring sensors 31. To avoid this, only one sensor 31 may be activated at a time, and so the signal provided by the detector array 19 at a particular time will correspond to the presence or absence of the analyte corresponding to that particular sensor 31.

Embodiments of the invention may be provided in which a sensor array 16 has independently addressable sensors 31 so that only those sensors 31 that are of interest at a particular time may be turned on. The sensor controller 13 may be used to turn sensors 31 on and off at desired times. Further, the detector array 19 may be comprised of independently addressable detectors 43, so that only those detectors 43 that are of interest at a particular time may be turned on. For example, the sensor controller 13 may be used to turn detectors 43 on and off at desired times so that a sensor 31 and its corresponding detector 43 are turned on at the same time and turned off at the same time. However, it should be noted that the invention may be implemented via a detector array 19 comprised of detectors 43 which are not independently addressable.

Each sensor 31 may be turned on selectively by applying a voltage at a particular location (see for example, Jiang, H. X., Jin, S. X., Li, J., Shakya, J., and Lin, J. Y., "III-nitride blue microdisplays," Applied Physics Letters, 2001 78(9) p. 1303-1305; Ozden, I., Diagne, M., Nurmikko, A. V., Han, J., and Takeuchi, T., "A matrix addressable 1024 element blue light emitting InGaN QW diode array," Physica Status Solidi a-Applied Research, 2001 188(1) p. 139-142). The controlling circuitry for the sensor array 16 may be on the same integrated circuit ("IC") as the detector array 19, or on a separate controlling IC. Each sensor 31 may be activated by applying a DC voltage for a particular length of time, $t_{on}$. Alternatively, the voltage applied to each sensor 31 may be modulated at some frequency, $f_{mod}$, which may also allow each sensor 31 to exhibit its own, unique modulation frequency. Using a DC voltage may allow for amplitude information to be obtained, while modulating the voltage applied to a sensor 31 may allow for phase measurements.

Figure 5:
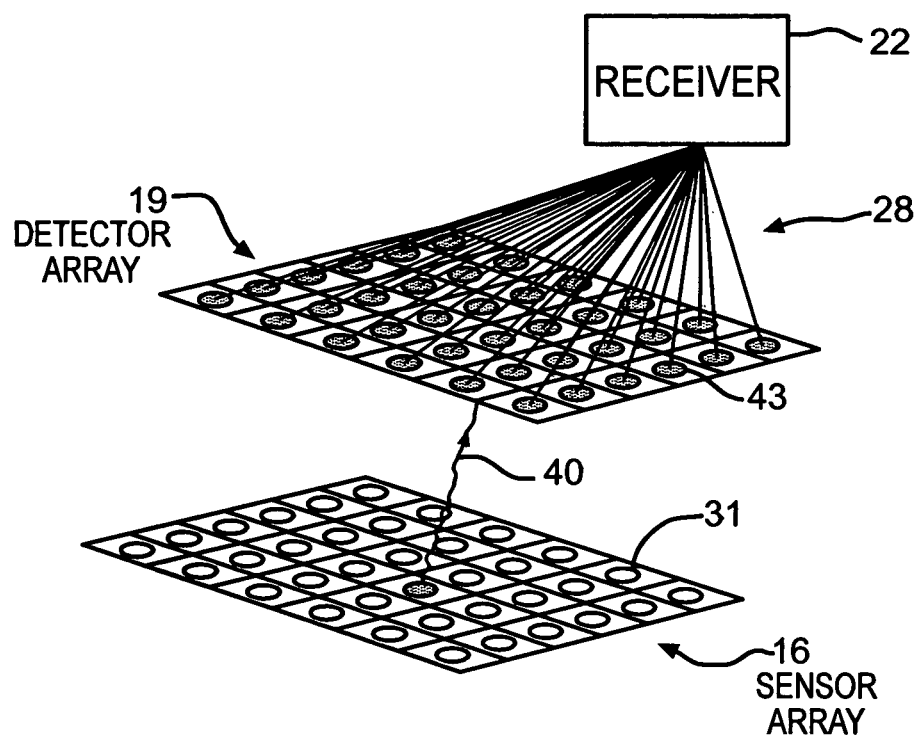
FIG. 5, which is a diagram illustrating features of an embodiment of the invention in which one sensor is activated, and the response from all detectors provide an output signal sent to the receiver.
Figure 6:
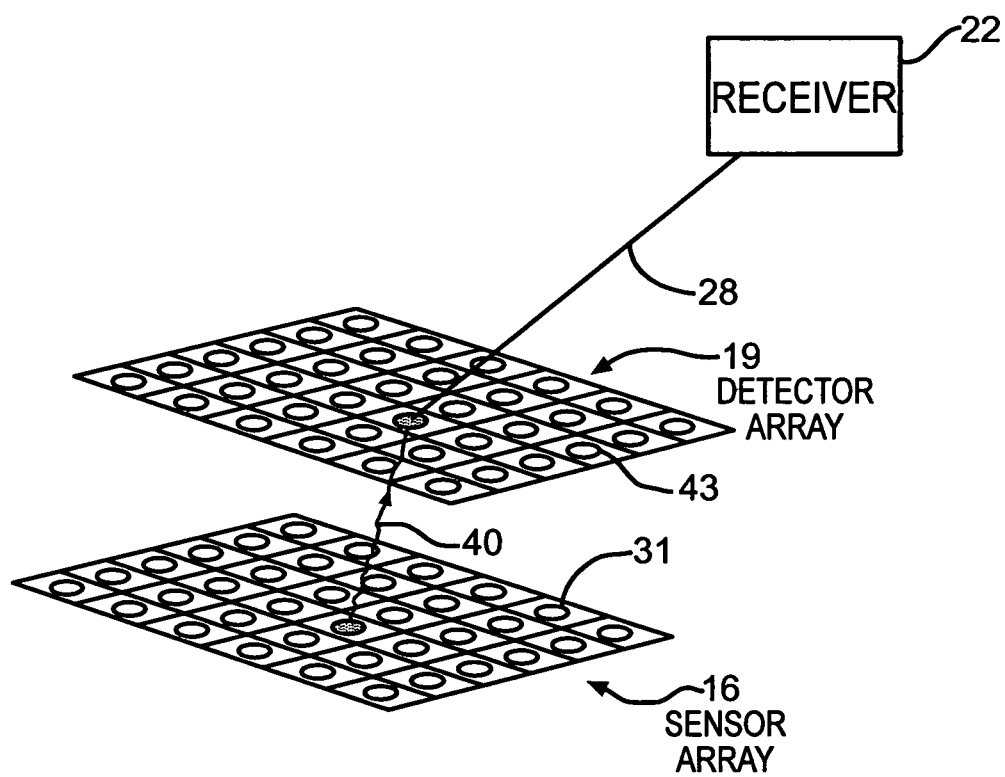
FIG. 6, which is a diagram illustrating features of an embodiment of the invention in which one sensor is activated and one detector is activated at the same time.

Having provided a general overview, two example embodiments of the invention will be considered. In the first example, one sensor 31 is activated at a time, and the responses of all detectors 43 are combined to obtain one output signal provided to the receiver 22. FIG. 5 depicts the sensor 31 and detectors 43 that are active in this first example at a particular instant of time by blackening the location of the active sensor 31 and active detectors 43. In this example, alignment of the sensor array 16 with the detector array 19 may be relatively simple, since precise alignment is not necessary. In a second example, one sensor 31 and its corresponding detector 43 are activated at a time, and the output signal from the detector 43 is provided to the receiver 22. FIG. 6 depicts the sensor 31 and detector 43 that are active in this second embodiment at a particular instant of time by blackening the location of the active sensor 31 and active detector 43. This example embodiment of the invention may use less power because only one detector circuit is active at a time, but better alignment than the previously described first example may be needed.

Both examples may use a sensor array 16 that has addressable sensors 31, and both examples may have the sensor compounds 37 formed directly on LEDs 34. Methods of forming the sensor compounds 37 on the LEDs 34 may include those disclosed by E. J. Cho, F. V. Bright, "Integrated Chemical Sensor Array Platform Based on a Light Emitting Diode, Xerogel-Derived Sensor Elements, and High-Speed Pin Printing," Analytica Chimica Acta, vol. 470, pp. 101-110, 2002). In both examples, the LEDs 34 may be sequentially turned on by the sensor controller 13. The timing associated with sequentially turning on the LEDs 34 may be used by the receiver 22 to identify portions of the output signal being provided to the receiver 22. For example, time-slicing may be used to correlate a portion of the output signal with a particular sensor 31.

A filter 46 may be used to augment the ability of the detector array 19 to receive energy 40 that is of interest. A narrow-band optical filter 46 may be included for this purpose. For example, if a sensor compound 37 is known to fluoresce at a particular wave length, then it may be beneficial to filter the energy 40 emanating from that sensor 31 so as to attenuate other wavelengths. By using a filter 46, the ability of a detector 43 to receive energy emanating from its corresponding sensor 31 may be improved. By attenuating unwanted wavelengths, the detector 43 should be more likely to provide an output signal to the receiver 22 that properly indicates the state of the sensor 31. Further, a filter 46 may reduce or eliminate the chance that a detector 43 will sense energy 40 from a sensor 31 that does not correspond to that detector 43. A filter 46 may be provided to filter energy 40 from one sensor 31, a group of sensors 31 or all sensors 31 in the sensor array 16. The filter 46 may be electrically tunable, such as a short cavity Fabry-Perot filter, and in this manner, the filter characteristics may be altered.

Figure 7:
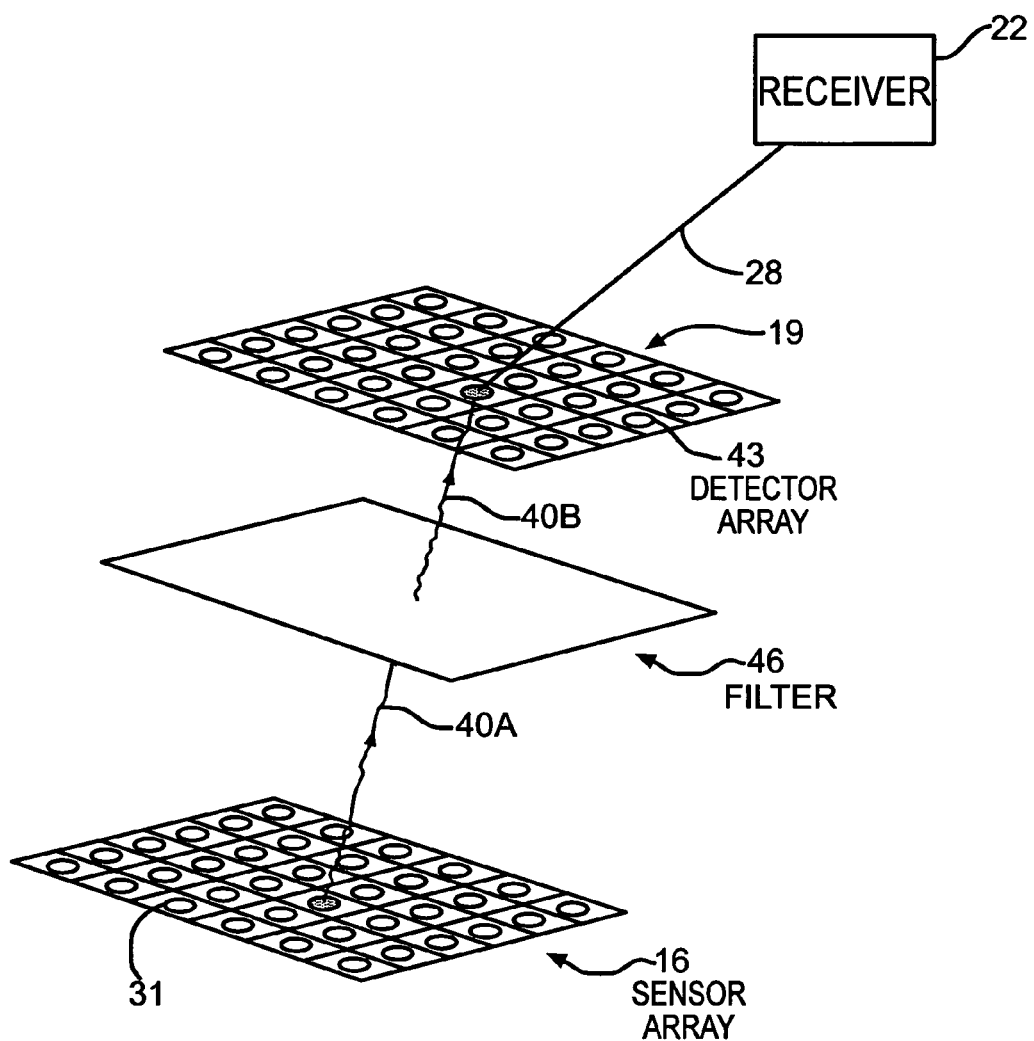
FIG. 7, which is a diagram of a device according to the invention having a filter.

FIG. 7 shows a first configuration according to the invention in which a single large area electrically tunable filter 46 is placed between the sensor array 16 and the detector array 19. Unfiltered energy 40A is received by the filter 46, and filtered energy 40B leaves the filter. Adjustments to the filter 46 may be timed to coincide with the particular sensor 31 that is turned on. For example, when a first sensor 31 is turned on, the filter's characteristics may be adjusted to attenuate electromagnetic energy that may interfere with detection of fluorescence by the first sensor's 31 sensor compound 37. Then, when a second sensor 31 is turned on, the filter's characteristics may be adjusted again to attenuate a different wavelength that may interfere with detection of fluorescence by the second sensor's 31 sensor compound 37.

Figure 8:
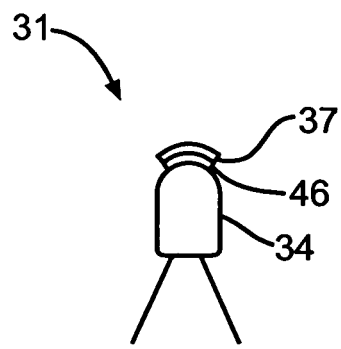
FIG. 8, which illustrates a sensor having a filter that may be used in a device according to the invention.
Figure 9:
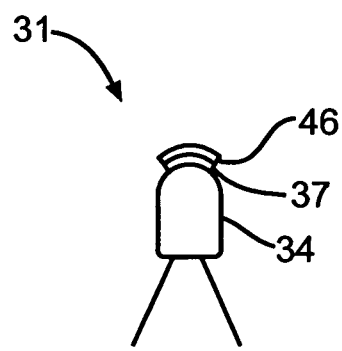
FIG. 9, which illustrates a sensor having a filter that may be used in a device according to the invention.

In a second configuration of a device having a filter, each sensor needing a filter may be provided with an integral filter. The filter may be formed on the sensor between the LED and the sensor compound (see FIG. 8), or the filter may be formed on the sensor so as to reside between the sensor compound and the detector array (see FIG. 9). This second configuration may be implemented in a manner which does not require adjusting the filter characteristics to match the particular sensor 31 that is turned on.

Figure 10:
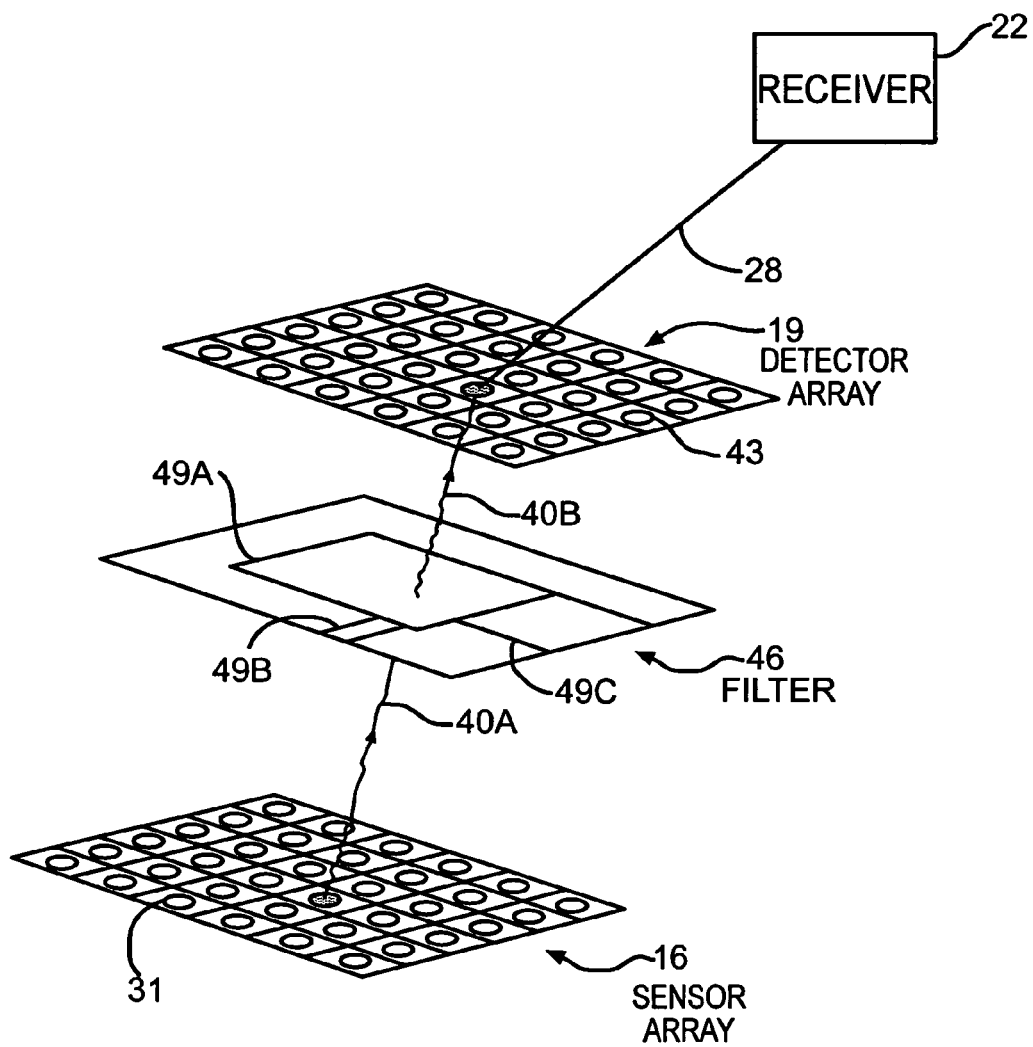
FIG. 10, which is a diagram of a device according to the invention having a filter.

In a third configuration of a device having a filter 46, an array of filter elements 49A, 49B, 49C may be placed between the sensor array and the detector array. One implementation of this configuration would be to provide a filter array having a first filter element 49A that serves to attenuate electromagnetic energy from a first group of sensors, and a second filter element 49B that serves to attenuate electromagnetic energy from a second group of sensors. FIG. 10 depicts such an arrangement. This configuration may reduce the number of filters 46 that are needed, and may reduce or eliminate the number of adjustments to the filter 46 in order to match the particular sensor 31 that is turned on.

Figure 11:
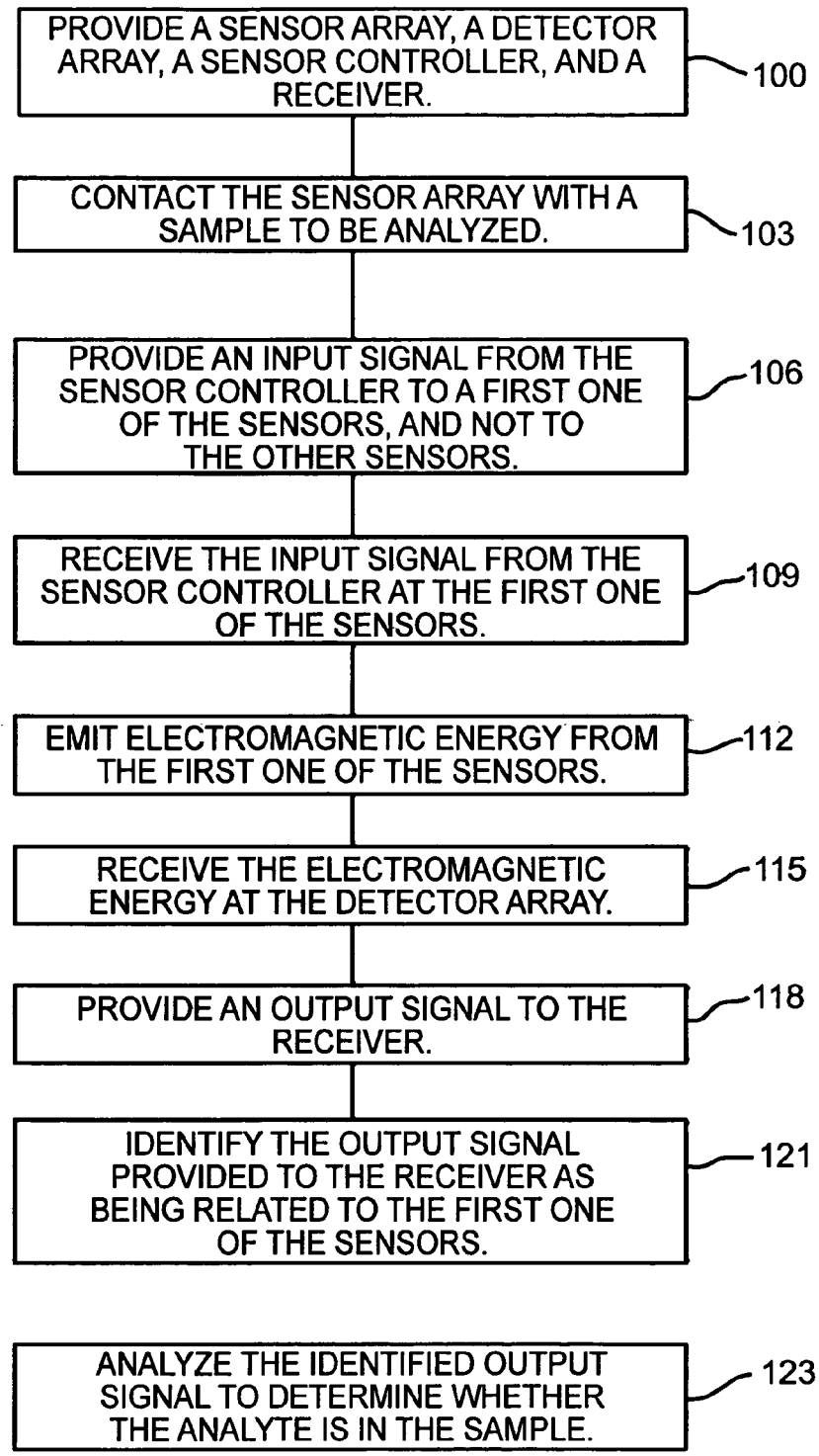
FIG. 11, which illustrates a method according to the invention.

FIG. 11 shows steps of a method according to the invention. Such a method may be used to determine whether an analyte is in a sample. Such a method may begin by providing 100 (a) a sensor array having a plurality of sensors, each sensor being responsive to a different analyte of interest, and each sensor being able to emit electromagnetic energy, (b) a detector array having a plurality of detectors, each detector being able to receive electromagnetic energy emitted from the sensor array, (c) a sensor controller in communication with the sensor array, and (d) a receiver in communication with the detector array. The sensor array may be contacted 103 by the sample, and an input signal from the sensor controller may be provided 106 to a first one of the sensors so as to activate only that sensor. The first one of the sensors may receive 109 the input signal from the sensor controller and emit 112 electromagnetic energy. The emitted electromagnetic energy may be received 115 at the detector array, which then may provide 118 an output signal, which corresponds to the emitted electromagnetic energy, to the receiver. The receiver may identify 121 the output signal as being related to the first one of the sensors, and analyze 123 the output signal to determine whether the analyte is in the sample.

After the first one of the sensors emits electromagnetic energy, the first one of the sensors may be turned off by the sensor controller, and a second one of the sensors may receive an input signal from the sensor controller, so as to activate only the second sensor. The steps identified above as steps 112 through 123 may be performed with respect to the second sensor. After the second sensor emits electromagnetic energy, the process may be repeated with other sensors in the sensor array. In this fashion, the sample may be tested for a plurality of analytes using a single device and in a short amount of time.

In an embodiment of the method, the signal provided to the receiver may correspond to more than one of the detectors (see FIG. 2). Alternatively, the signal provided to the receiver may correspond to only one of the detectors (see FIG. 3).

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A detection device, comprising:
  a sensor array having a plurality of independently addressable sensors, each sensor being responsive to a different analyte of interest, and each sensor being able to exhibit characteristics upon applying a voltage to its address, the exhibited characteristics not being present until the application of electromagnetic energy;
  a detector array having a plurality of independently addressable detectors, a first one of the detectors being able to detect the exhibited characteristics from a first one of the sensors, a second one of the detectors being able to detect the exhibited characteristics from a second one of the sensors, and a third one of the detectors being able to detect the exhibited characteristics from a third one of the sensors; and
  a sensor controller in communication with the sensor array, and using the addresses of the sensor is able to turn on at least one of the sensors so as to exhibit characteristics that are not present until the application of electromagnetic energy while another of the sensors is turned off so as not to exhibit characteristics, those exhibited characteristics not being present until the application of electromagnetic energy.

2. The detection device of claim 1, wherein the sensor controller turns on one sensor at a time.

3. The detection device of claim 1, further comprising a receiver in communication with the detector array.

4. The detection device of claim 3, wherein the receiver obtains signals from all the detectors when a sensor is turned on.

5. The detection device of claim 3, wherein the receiver obtains a signal from a first one of the detectors only when a particular sensor is turned on.

6. The detection device of claim 1, wherein the sensor array includes light emitting diodes able to emit the electromagnetic energy.

7. The detection device of claim 1, wherein the sensor array includes xerogels, each xerogel having a sensor compound that is responsive to a different analyte of interest.

8. The detection device of claim 1, further comprising a filter able to receive the electromagnetic energy and able to allow a first portion of the energy to pass through the filter to a greater degree than a second portion of the energy.

9. The detection device of claim 8, wherein the filter is tunable so as to modify which portion of the energy is the first portion.

10. The detection device of claim 1, further comprising a filter formed on one of the sensors.

11. A method of determining whether an analyte is in a sample, comprising:
   providing (a) a sensor array having a plurality of independently addressable sensors, each sensor being responsive to a different analyte of interest, and each sensor being able to exhibit characteristics upon applying a voltage to its address, the exhibited characteristics not being present until the application of electromagnetic energy, (b) a detector array having a plurality of independently addressable detectors, each detector being able to detect the exhibited characteristics of a sensor, (c) a sensor controller in communication with the sensor array, and (d) a receiver in communication with the detector array;
   contacting the sensor array with a sample to be analyzed;
   providing an input signal from the sensor controller to an address of a first one of the sensors, and not providing a signal to addresses of others of the sensors;
   receiving the input signal at the first one of the sensors;
   exhibiting characteristics that are not present until the application of electromagnetic energy from the first one of the sensors;
   detecting the exhibited characteristics at the detector array;
   providing an output signal from the detector array to the receiver;
   identifying the output signal as being related to the first one of the sensors;
   analyzing the identified output signal to determine whether the analyte is in the sample.

12. The method of claim 11, wherein the signal provided to the receiver corresponds to more than one of the detectors.

13. The method of claim 11, wherein the signal provided to the receiver corresponds to only one of the detectors.

* * * * *